United States Patent
Robinson et al.

(10) Patent No.: US 11,332,419 B2
(45) Date of Patent: May 17, 2022

(54) HYDROTHERMAL PRODUCTION OF ALKANES

(71) Applicants: Kirtland Robinson, Tempe, AZ (US); Ian Gould, Phoenix, AZ (US); Christiana Bockisch, Tempe, AZ (US); Everett Shock, Scottsdale, AZ (US); Hilairy Hartnett, Phoenix, AZ (US); Lynda B. Williams, Tempe, AZ (US)

(72) Inventors: Kirtland Robinson, Tempe, AZ (US); Ian Gould, Phoenix, AZ (US); Christiana Bockisch, Tempe, AZ (US); Everett Shock, Scottsdale, AZ (US); Hilairy Hartnett, Phoenix, AZ (US); Lynda B. Williams, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/038,602

(22) Filed: Sep. 30, 2020

(65) Prior Publication Data
US 2021/0107847 A1    Apr. 15, 2021

Related U.S. Application Data

(60) Provisional application No. 62/915,334, filed on Oct. 15, 2019.

(51) Int. Cl.
| | |
|---|---|
| *C07C 5/00* | (2006.01) |
| *C07C 5/03* | (2006.01) |
| *C07C 1/24* | (2006.01) |
| *B01J 23/755* | (2006.01) |

(52) U.S. Cl.
CPC ............... *C07C 5/03* (2013.01); *B01J 23/755* (2013.01); *C07C 1/24* (2013.01); *C07C 2523/745* (2013.01); *C07C 2523/755* (2013.01)

(58) Field of Classification Search
CPC .... C07C 5/03; C07C 1/24; C07C 2/08; C07C 11/02; C07C 11/09; C07C 13/18; C07C 9/21; C07C 2523/745; C07C 2523/755; B01J 23/755
See application file for complete search history.

(56) References Cited

U.S. PATENT DOCUMENTS

| | | | |
|---|---|---|---|
| 5,877,372 A * | 3/1999 | Evans | ........................ C07C 2/06 585/510 |
| 8,188,327 B1 | 5/2012 | Bakshi | |
| 2021/0230088 A1 | 7/2021 | Loescher et al. | |

OTHER PUBLICATIONS

Anderson et al., "Mutual solubilities and vapor pressures for binary and ternary aqueous systems containing benzene, toluene, m-xylene, thiophene and pyridine in the region 100-200° C.," Fluid Phase Equilibria, 1986, 32(1):63-76.

(Continued)

*Primary Examiner* — Sharon Pregler
(74) *Attorney, Agent, or Firm* — Fish & Richardson P.C.

(57) ABSTRACT

Synthesizing an alkane includes heating a mixture including an alkene and water at or above the water vapor saturation pressure in the presence of a catalyst and one or both of hydrogen and a reductant, thereby hydrogenating the alkene to yield an alkane and water, and separating the alkane from the water to yield the alkane. The reductant includes a first metal and the catalyst includes a second metal.

22 Claims, 4 Drawing Sheets

(56) References Cited

OTHER PUBLICATIONS

Bockisch et al., "Kinetics and Mechanisms of Dehydration of Secondary Alcohols Under Hydrothermal Conditions," ACS Earth and Space Chemistry, 2018, 2(8):821-832.

Bockisch et al., "Selective hydrothermal reductions using geomimicry," Green Chemistry, 2019, 21(15):4159-4168.

Brown et al., "Liquid-Liquid Equilibria for Binary Mixtures of Water + Acetophenone, + 1-Octanol, + Anisole, and + Toluene from 370 K to 550 K," Journal of Chemical & Engineering Data, Aug. 23, 2000, 45(5):846-850.

Busca, Guido, "Acid Catalysts in Industrial Hydrocarbon Chemistry," Chem. Rev., 2007, 107(11):5366-5410.

Fecteau et al., "Production of Carboxylic Acids from Aldehydes under Hydrothermal Conditions: A Kinetics Study of Benzaldehyde," ACS Earth and Space Chemistry, 2019 (Available online Dec. 11, 2018, prior to the formal issue date), 3:170-191.

Goortani et al., "Production of Isooctane from Isobutene: Energy Integration and Carbon Dioxide Abatement via Catalytic Distillation," Industrial & Engineering Chemistry Research, 2015, 54(14):3570-3581.

Kumar et al., "Alkylation of Raffinate II and Isobutane on Nafion Silica Nanocomposite for the Production of Isooctane," Energy & Fuels, 2006, 20(2):481-487.

Heger et al., "The Static Dielectric Constant of Water at High Pressures and Temperatures to 500 MPa and 550 C," Ber. Bunsenges. Phys. Chem., 1980, 84(8):758-762.

Robinson et al., "Deamination reaction mechanisms of protonated amines under hydrothermal conditions," Geochimica et Cosmochimica Acta, 2019 (Available online Sep. 28, 2018, prior to the formal issue date), 244:113-128.

Seewald, Jeffrey S., "Evidence for metastable equilibrium between hydrocarbons under hydrothermal conditions," Nature, Jul. 28, 1994, 370(6487): 285-287.

Shipp et al., "Organic functional group transformations in water at elevated temperature and pressure: Reversibility, reactivity, and mechanisms," Geochimica et Cosmochimica Acta, 2013 (Available online Nov. 28, 2012, prior to the formal issue date), 104:194-209.

Shipp et al., "Sphalerite is a geochemical catalyst for carbon-hydrogen bond activation," PNAS, Aug. 12, 2014, 111(32):11642-11645.

Shock et al., "Thermodynamics of Organic Transformations in Hydrothermal Fluids," Reviews in Mineralogy and Geochemistry, 2013, 76(1):311-350.

Shock et al., "Earth as Organic Chemist," In: Deep Carbon: Past to Present, Deep Carbon Observatory, University of Cambridge Press, 2019, 14:415-446.

Sweeton et al., (1974). "Acidity Measurements at Elevated Temperatures. VII. Dissociation of Water, Journal of Solution Chemistry, 1974, 3(3):191-214".

Xu et al., "Kinetics and Mechanism of Isobutene Formation from T-Butanol in Hot Liquid Water," AIChE Journal, Sep. 1994, 40(9):1524-1534.

Yang et al., "The central role of ketones in reversible and irreversible hydrothermal organic functional group transformations," Geochimica et Cosmochimica Acta, 2012, 98:48-65.

Yang et al., "Hydrothermal Photochemistry as a Mechanistic Tool in Organic Geochemistry: The Chemistry of Dibenzyl Ketone," The Journal of Organic Chemistry, 2014, 79(17):7861-7871.

Yang et al., "Organic Oxidations Using Geomimicry," TheJournal of Organic Chemistry, 2015, 80(24):12159-12165.

nsf2026imgallery.skild.com [online], "Geomimicry," upon information and belief, available no later than Jun. 19, 2019, retrieved on May 6, 2021, retrieved from URL <https://web.archive.org/web/20190614021812/https://nsf2026imgallery.skild.com/entries/geomimicry>, 2 pages.

\* cited by examiner

HYDROTHERMAL PRODUCTION OF ALKANES

CROSS-REFERENCE TO RELATED APPLICATION

This application claims the benefit of U.S. Patent Application No. 62/915,334 filed on Oct. 15, 2019, which is incorporated by reference herein in its entirety.

STATEMENT OF GOVERNMENT SUPPORT

This invention was made with government support under NNX16AO82G awarded by the National Aeronautical & Space Administration. The government has certain rights in the invention.

TECHNICAL FIELD

This invention relates to hydrothermal production of alkanes.

BACKGROUND

Isooctane (2,2,4-trimethylpentane) is an important ingredient in hydrocarbon fuels that power cars, airplanes, and other machinery. Because of this, it is highly relevant to the transportation, manufacturing, and construction industries. One conventional method by which isooctane can be synthesized is a process called alkylation that uses large quantities of sulfuric acid or hydrofluoric acid to dimerize isobutane and isobutene. This method generates toxic waste that is costly to remediate. Another conventional way to synthesize isooctane is to dimerize isobutene to isooctene (2,2,4-trimethyl-2-pentene) with a supported acid catalyst, followed by hydrogenation with one of several metal hydrogenation catalysts (e.g., platinum or palladium). The supported acid catalysts generate costly waste, and the metal catalysts are rare materials and therefore expensive.

SUMMARY

Hydrothermal production of alkanes described herein involve water, Earth-abundant materials, heat, and a reaction vessel that can withstand moderate pressures. As such, these methods are low in cost and free of toxic waste.

Synthesizing an alkane includes heating a mixture including an alkene and water at or above the water vapor saturation pressure in the presence of a catalyst and one or both of hydrogen and a reductant, thereby hydrogenating the alkene to yield an alkane and water, and separating the alkane from the water to yield the alkane. The reductant includes a first metal and the catalyst includes a second metal.

Implementations of the general aspect can include one or more of the following features.

In some cases, the alkene is a second alkene and the mixture is a second mixture, a first alkene is combined with water to yield a first mixture, and the first mixture is heated above atmospheric pressure to yield the second mixture including the second alkene.

The general aspect can include dehydrating an alkyl alcohol having at least two carbons to yield the first alkene. Examples of suitable alcohols include butanol (e.g., tert-butanol or isobutanol). In one example, the first alkene is isobutene, the second alkene is isooctene, and the alkane is isooctane.

Heating the first mixture at or above the water vapor saturation pressure can include heating the first mixture to a temperature in a range of 250° C. to 350° C., a pressure in a range of 40 bar to 165 bar, or both. Heating the first mixture and the second mixture typically includes heating the first mixture in a first reactor and heating the second mixture in a second reactor. In some cases, the second mixture is transferred from the first reactor to the second reactor. In other cases, the first reactor and the second reactor are the same reactor, and no transfer occurs. Heating the second mixture typically includes heating to a temperature in a range 250° C. to 300° C.

The first metal oxidizes in water to yield one or more oxides of the first metal. In some cases, the first metal oxidizes in water to further yield molecular hydrogen. In certain cases, the first metal includes iron. The second metal remains substantially unoxidized. The second metal catalyzes the reduction of the second alkene with molecular hydrogen to yield the alkane. In one example, the second metal includes nickel.

Isolating the alkane from the water can be performed by mechanical separation (e.g., decanting, skimming, and the like).

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

Figure 1:
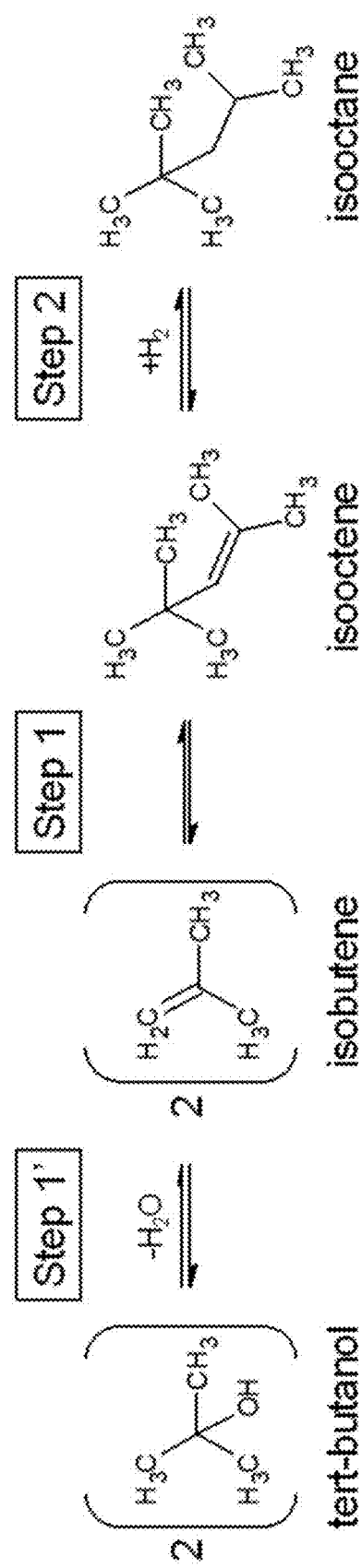
FIG. 1 depicts a reaction scheme showing synthesis of isooctane as described herein.

Methods described in this disclosure include reduction (hydrogenation) of carbon-carbon π-bonds using i) hydrogen, a first metal as a reductant to reduce water to hydrogen, or both; and ii) a second metal as a catalyst in water as a solvent at a hydrothermal temperature (e.g., at least 200° C. at or above the saturated water vapor pressure). Methods described in this disclosure include reduction of an alkene using a first metal as a reductant and a second metal as a catalyst in water as a solvent at a hydrothermal temperature (e.g., at least 200° C. at the saturated water vapor pressure). Circumneutral, hot water is used as the solvent, and no additional acid or base catalysts are required. The resulting alkene is reduced to a corresponding alkane using inexpensive Earth-abundant reagents and catalysts rather than rare and expensive metal catalysts typically employed, such as platinum or palladium. The use of circumneutral water as the solvent contributes to a process that is less hazardous than other methods that employ volatile, toxic, and/or flammable solvents. Since this reaction requires no added acids, bases, or other aqueous reagents, the water can be recycled for use in future synthesis reactions, and produces no toxic waste requiring remediation. Other applications include replacing hazardous acids with hydrothermal water, as well as replacing high-cost catalysts with Earth-abundant ones in chemical manufacturing processes.

In some implementations, synthesizing an alkane includes heating a mixture including an alkene and water at or above the water vapor saturation pressure in the presence of i) hydrogen, a reductant to reduce water to hydrogen, or both; and ii) a catalyst, thereby hydrogenating the alkene to yield an alkane. In one example, the alkene includes cyclohexene and the alkane includes cyclohexane.

In some implementations, the alkene is a second alkene and the mixture is a second mixture. A first alkene is combined with water to yield a first mixture, and the first mixture is heated at or above the water vapor saturation pressure to yield the second mixture including the second alkene. The second alkene is typically formed in the absence of the metal reductant and the metal catalyst. In one example, the first alkene includes isobutene, the second alkene includes isooctene, and the alkane includes isooctane.

In certain implementations, alkane synthesis includes dimerization of a first alkene to yield a second alkene, and reduction of the second alkene to yield an alkane. In some cases, the first alkene and the second alkene react to yield a third alkene, and the third alkene is reduced (hydrogenated) to yield an alkane. In certain cases, the first alkene is prepared by dehydration of an alkene precursor (e.g., an alcohol).

In some implementations, an alcohol or its corresponding alkene is loaded into a first reactor that contains water to yield a first mixture. The first reactor is typically a pressure vessel capable of withstanding 350 bar. The first mixture is heated to subcritical temperatures (e.g., at least about 200° C., or about 200° C. to about 350° C.) for a length of time in a range of about 1 to about 100 hours. Respective pressures that result from the liquid-vapor equilibrium ($P_{sat}$) of water are in a range of 16 bar to 165 bar. Under pressure and heating characteristic of subcritical hydrothermal conditions (e.g., at least about 200° C., or about 200° C. to about 350° C. and $P_{sat}$), the alcohol dehydrates, the alkene dimerizes, or both to yield a second mixture.

In some cases, the second mixture is transferred to a second reactor. The second reactor is typically a vessel capable of withstanding pressure of at least about 350 bar. In certain cases, a single reactor functions as the first reactor and the second reactor, such that transfer from the first reactor to the second reactor is not required.

The second mixture is contacted with i) hydrogen, a solid reagent, or both; and ii) a solid catalyst. The second mixture is heated to a temperature in a range of 250° C. to 350° C. for a length of time in a range of 24 to 96 hours. Suitable solid reagents and solid catalysts include native metals (i.e., metals found in pure metallic form in nature, rather than oxidized metals derived from ore). One example of a suitable reagent-catalyst combination includes a first native metal (a metal reductant) that oxidizes in water to yield one or more oxides and a second native metal (a metal catalyst) that remains substantially unoxidized in water. Oxidation of the metal reductant by water to yield metal oxides results in the generation of molecular hydrogen from the reduction of water. In some implementations, hydrogen is added in place of or together with the metal reductant. The metal catalyst, which remains substantially unoxidized, catalyzes the reduction of the dimerized alkene with molecular hydrogen to yield a third mixture including an alkane. In one example, the metal reductant is native iron, and the metal catalyst is native nickel. The metal reductant is typically present in a molar ratio of at least about 4:1 with respect to the alkene. The metal reductant is also typically present in a molar ratio of at least about 4:1 with respect to the metal catalyst.

The third mixture is allowed to cool (e.g., to room temperature). The organic (alkane-containing) phase is separated (e.g., mechanically separated) from the aqueous phase to yield an alkane.

The use of hydrothermal water (e.g., water in the liquid state at a temperature of at least about 200° C.) in the first reactor facilitates the synthesis process. The $pK_a$ of $H_2O$ at 250° C. (at liquid/vapor saturation pressure, $P_{sat}$=40 bar) is ~11. This results in a neutral pH of about 5.5, which enhances the kinetics of acid-catalyzed reactions (e.g., alcohol dehydration, alkene dimerization). Under these same hydrothermal conditions, the dielectric constant of $H_2O$ lies between that of methanol and acetone at ambient conditions (25° C., 1 bar), due at least in part to a decrease in hydrogen bonding at higher temperatures. Thus, the solubility of organic compounds in water increases with increasing temperature, which means that hydrothermal fluid represents an appropriate solvent for organic chemical reactions. For example, the solubility constant ($K_{sol}$) for toluene in water is ~$10^{-2.2}$ at 25° C., but increases to ~$10^{-0.5}$ at 250° C.; this translates roughly to a saturation change from 0.006 to ~0.3 molal toluene. High temperatures also facilitate faster reaction kinetics during synthesis reactions, avoiding the need for highly reactive reagents or additional catalysts. Solution chemistry occurs readily in the hydrothermal water, and the hydrocarbon products form a separate phase that can be mechanically extracted upon cooling, due to changes in solubility with temperature. Hydrogen is also generated from certain native metals (e.g., iron) under hydrothermal conditions and metals (e.g., nickel) that are otherwise typically inert become activated as hydrogenation catalysts.

Unlike conventional organic solvents, water is low in cost and is not toxic, volatile, or flammable. Furthermore, the water used in this synthesis is circumneutral (e.g., having a pH in a range of about 5 to about 9, about 5.5 to about 8.5, about 6 to about 8, or about 7 at room temperature), with no added aqueous reagents. Water can also be mechanically separated from the organic products upon cooling from hydrothermal reaction temperatures, and reused for future reactions. Moreover, disposal of water is routine, unlike the disposal of carcinogenic solvents and acidic sludge waste required for conventional methods.

The use of Earth-abundant metals (e.g., iron and nickel) for molecular hydrogen generation as well as hydrogenation catalysis is advantageous in several respects. These metals are low in cost, and can be disposed of cheaply and routinely and replaced with fresh and high-activity materials.

Synthesis methods described herein can be applied to improve hydrocarbon synthesis in chemical manufacturing (e.g., oil refinement.) In one example, isooctane—conventionally produced via alkylation processes that require hazardous concentrated acids or produced using a supported acid catalyst and expensive metal hydrogenation catalysts—can be produced from similar chemical feedstocks by synthesis methods described herein without the need for hazardous and/or expensive materials, simply by using water, heat, and Earth-abundant materials. In one implementation, isooctane is synthesized according to the reaction scheme depicted in FIG. 1.

Experimental solutions were prepared with 18.2 MΩ deionized water, which was bubbled with ultra-high purity (≥99.999%) argon for ≥20 minutes to provide anoxic reaction conditions before being loaded into silica tubes sealed at one end (eventual reaction vessels). Silica tubes were purchased from GM Associates and Technical Glass Products as 2×6 mm (inner diameter×outer diameter) "fused quartz" (silica) tubing. Tert-butanol was added to reaction vessels used to test reaction Steps 1' and 1 (dehydration of tert-butanol to yield isobutene and dimerization of isobutene to yield isooctene, as depicted in FIG. 1), while isooctene, nickel, and iron, were added to experiments used to test reaction Step 2 (hydrogenation of isooctene to yield isooctane, as depicted in FIG. 1). Upon loading the materials, the tubes were immediately immersed in liquid nitrogen to freeze the reactant solution. To further provide anoxic reaction conditions, the tube headspace was briefly purged with argon, and the headspace was vacuum pumped to ≤100.0 millitorr to remove remaining atmospheric gases. Still submerged in liquid nitrogen above the height of the frozen reactants and under vacuum, the open ends of the tubes were sealed with a welding torch.

An oven was preheated with screw-capped iron pipes (to provide thermal inertia) to 250° C. for ≥2 hours. As verified by two Fluke 52 II thermocouples, the air temperature within the preheated iron pipes varied spatially and temporally by no more than ±2.5° C. Reaction vessels were placed inside the preheated iron pipes for the duration of the experiments. At the end of each experiment, the reaction vessels were quickly removed from the oven and submerged in room temperature water to quench the reactions and preserve the products. The time at which the reaction vessels were removed from the oven was considered the final experimental time.

Prior to extracting organic reaction products, the solutions were transferred to 7 mL Supelco clear glass vials with polytetrafluoroethylene/silicone septa lids. Dichloromethane, containing 0.01 M dodecane as an internal standard, was added to the solution in a 10:1 ratio for the liquid/liquid extraction procedure. This mixture was intermittently gently shaken for ≥15 minutes and the organic layer was separated and immediately taken for analysis.

Experiments and organic compound standards were analyzed using a Bruker Scion 456 Gas Chromatograph (GC), equipped with a Varian CP-8400 auto-sampler, Supelco Equity™-5 column (30 m×0.25 mm×0.5 µm capillary fused silica), and flame ionization detector (FIDs). For oven methods, peak assignment, and peak integration, Compass Chromatography Data System Version 3.0 Core Software was used. Response factors for isooctene and isooctane relative to a fixed concentration (0.01 M) of the internal standard, dodecane, were calculated from three-point linear calibration curves with $R^2 \geq 0.995$. Dichloromethane (DCM) was used as the solvent for all GC analyses. The GC method used an ultra-high purity (≥99.999%) helium:sample split ratio of 15:1 for all calibration standards and experiments. The oven temperature profile method is summarized in Table 1.

TABLE 1

GC oven heating method used for all calibration standards and experiments.

| T (° C.)[a] | Rate (° C./min)[b] | Hold (min)[c] |
|---|---|---|
| 40.0 | — | 0 |
| 140.0 | 10.0 | 0 |
| 220.0 | 5.0 | 0 |
| 300.0 | 20.0 | 5.0 |

[a]target heating temperatures for the oven

TABLE 1-continued

GC oven heating method used for all calibration standards and experiments.

| T (° C.)[a] | Rate (° C./min)[b] | Hold (min)[c] |
|---|---|---|

[b]rate of heating between target temperatures
[c]hold times at each target temperature Compound identification was achieved via comparison to standards using GC-FID for isooctene and isooctane, as well as analysis via gas chromatography-mass spectrometry (GC-MS) for isooctene, isooctane, and isooctene-1° (2,2,4-trimethyl-1-pentene). The GC-MS used was an Agilent 6890N GC 5973N single quadrupole MS at Arizona State University Core Research Facilities. Mass spectra were matched to the NIST17 database, and the highest match scores were reported.

Figure 2:
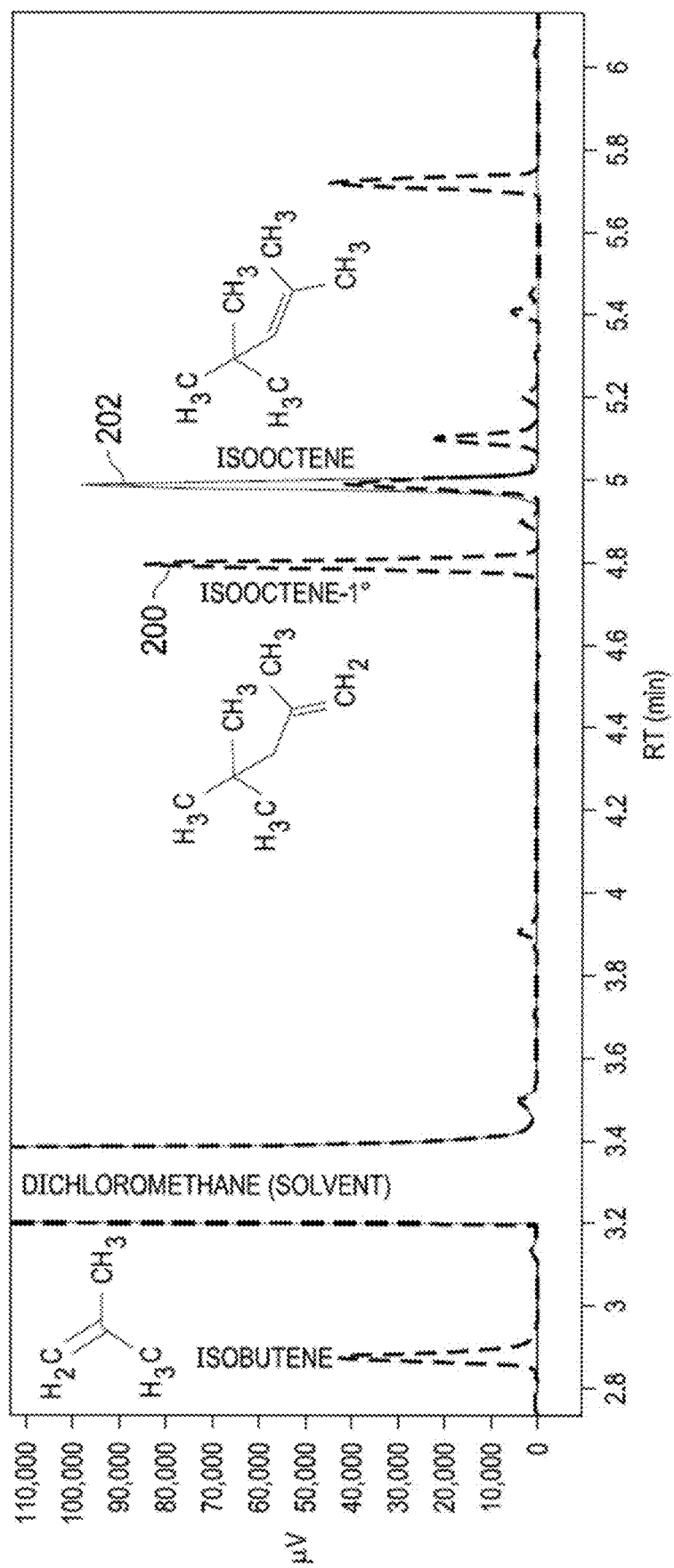
FIG. 2 shows gas chromatograms of the products of an isooctene synthesis reaction as depicted in FIG. 1 and an isooctene standard.

Hydrothermal experiments were performed to test whether isobutene would undergo dimerization to form isooctene (Step 1 in FIG. 1), and to test whether isooctene would undergo reduction to form isooctane (Step 2 in FIG. 1), the latter in the presence of iron and nickel. Following Steps 1' and 1 (FIG. 1), experiments begun with tert-butanol as a precursor to isobutene were observed to produce isobutene and isooctene. Plot 200 in FIG. 2 shows a GC-FID chromatogram for a hydrothermal experiment conducted with 0.5 M tert-butanol at 300° C. ($P_{sat}$) for 48 hours. Plot 202 is a separate chromatogram of an isooctene standard is overlaid for compound verification. In addition to standard comparison, isooctene and isooctene-1° were both identified via GC-MS. Isooctene-1° is an isomer of isooctene that presumably forms through hydration of isooctene to an alcohol followed by dehydration to the primary alkene. Both isooctene and isooctene-1° should be susceptible to reduction to isooctane. Their combined chemical yield was ~7% (no effort was made to optimize this yield). Isobutene was not verified via standard comparison or GC-MS due to analytical logistics. However, isobutene is very likely the attributed peak in FIG. 2 based on a comparison of retention times and boiling points between isobutene and the dichloromethane solvent.

Figure 3:
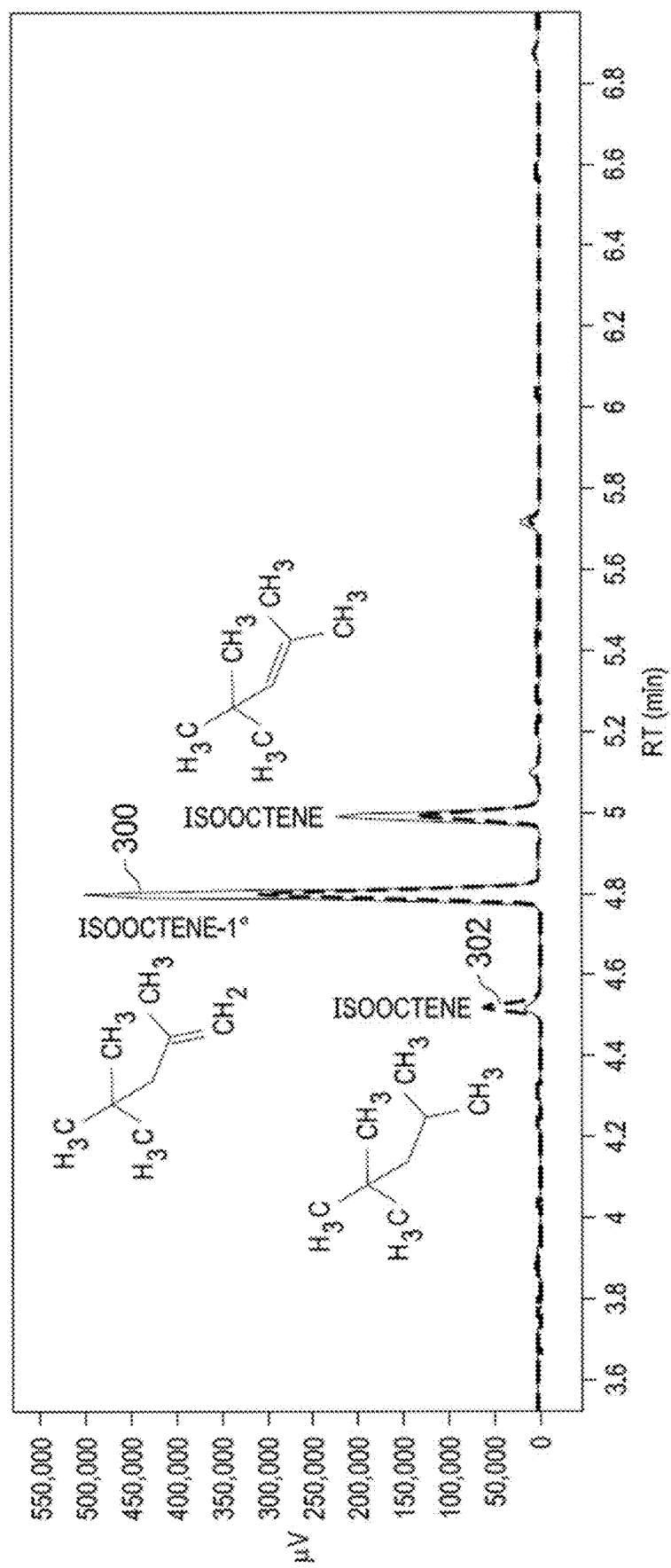
FIG. 3 shows gas chromatograms of the products of isooctane synthesis reactions as depicted in FIG. 1 after 31 hours and 48 hours.

In accordance with Step 2 (FIG. 1), experiments aimed at the reduction of isooctene were observed to produce isooctane. Plots 300 and 302 in FIG. 3 shows GC-FID chromatograms for hydrothermal experiments conducted with 0.2 M isooctene, 100 mg/mL iron, and 30 mg/mL nickel, at 250° C. ($P_{sat}$) for 31 hours and 48 hours, respectively. The product isooctane was verified by standard addition (not shown), and was also verified by GC-MS, in addition to GC-MS verification of the product isooctene-1° and the reactant isooctene. The chemical yield of isooctane increases from 31 to 48 hours, to ~6%, suggesting a potential to increase yields at longer timescales, or perhaps higher temperatures (no further optimization was performed). Isooctene-1° was produced in a similar ratio to isooctene at both 31 and 48 hours, as well as in experiments with tert-butanol as the initial reactant, suggesting that the primary alkene is in metastable equilibrium with the more substituted isooctene.

Figure 4:
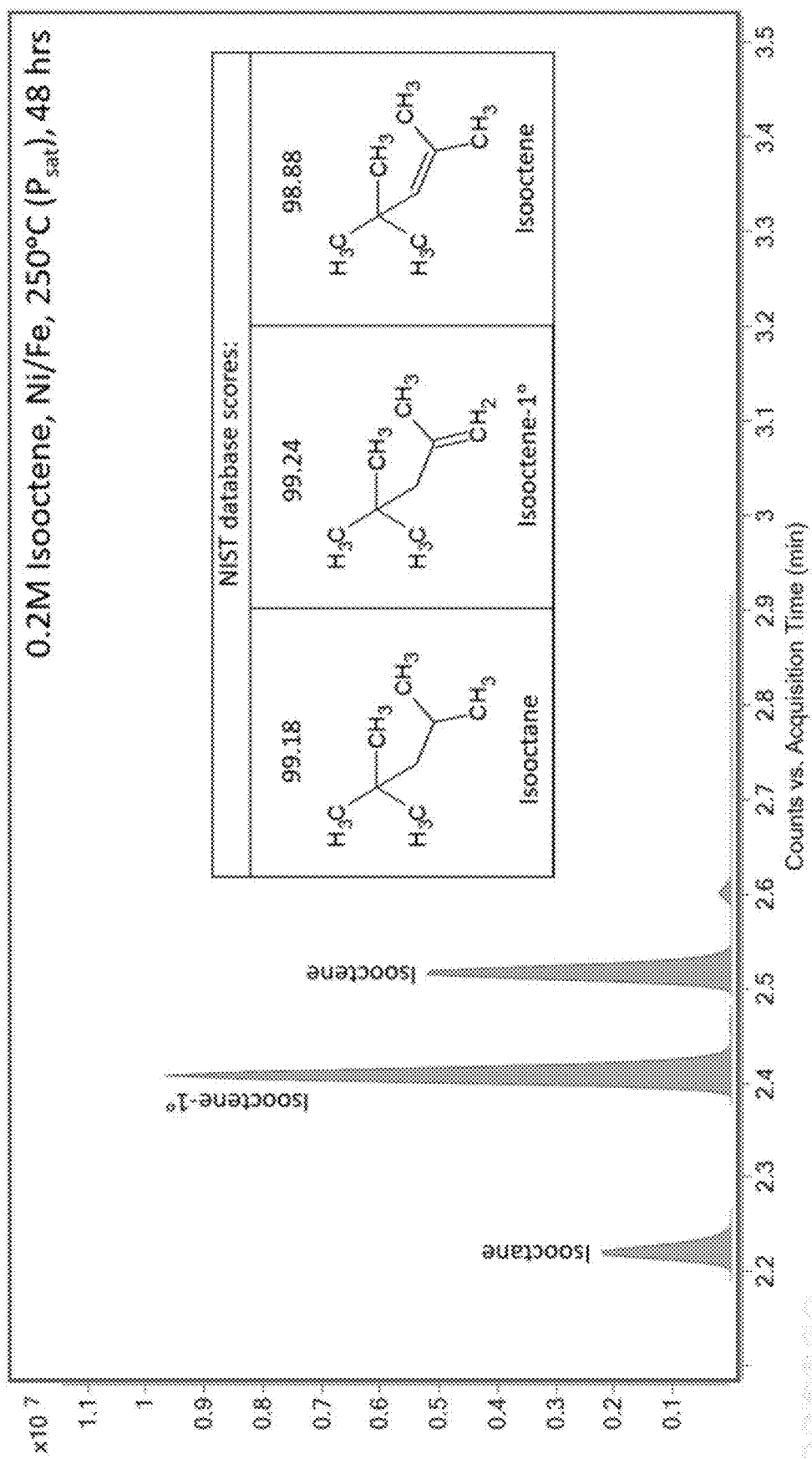
FIG. 4 shows a gas chromatography-mass spectrometry chromatogram of the products of an isooctane synthesis reaction as depicted in FIG. 1 after 48 hours. The inset shows reverse matching scores for the mass spectra of the compounds as compared to the NIST17 database.

The GC-MS chromatogram and compound identification results for the 48-hour isooctene reduction experiment are shown in FIG. 4. The matching scores for mass spectra of the peaks to isooctane, isooctene-1°, and isooctene in the NIST17 database provide confident identifications, especially because isooctane and isooctene were both verified by standard comparison.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of synthesizing an alkane, the method comprising:
    heating a mixture comprising an alkene and water at or above the water vapor saturation pressure in the presence of a catalyst and one or both of hydrogen and a reductant, thereby hydrogenating the alkene to yield an alkane and water, wherein the reductant comprises a first metal and the catalyst comprises a second metal; and
    separating the alkane from the water to yield the alkane, wherein heating the mixture comprises heating the mixture to a temperature in a range of 250° C. to 350° C. and at a pressure in a range of 40 bar to 165 bar.

2. The method of claim 1, wherein the alkene is a second alkene and the mixture is a second mixture, and further comprising:
    combining a first alkene and water to yield a first mixture; and
    heating the first mixture above atmospheric pressure to yield the second mixture, wherein the second mixture comprises the second alkene.

3. The method of claim 2, further comprising dehydrating an alkyl alcohol having at least two carbon atoms to yield the first alkene.

4. The method of claim 3, wherein the alcohol comprises butanol.

5. The method of claim 4, wherein the butanol comprises tert-butanol.

6. The method of claim 4, wherein the butanol comprises isobutanol.

7. The method of claim 2, wherein the first alkene comprises isobutene.

8. The method of claim 2, wherein the second alkene comprises isooctene.

9. The method of claim 1, wherein the alkane comprises isooctane.

10. The method of claim 2, wherein heating the first mixture above atmospheric pressure comprises heating the first mixture to a temperature in a range of 250° C. to 350° C.

11. The method of claim 2, wherein heating the first mixture above atmospheric pressure comprises heating the first mixture at a pressure in a range of 40 bar to 165 bar.

12. The method of claim 2, wherein heating the first mixture occurs in a first reactor, and heating the second mixture occurs in a second reactor.

13. The method of claim 12, comprising transferring the second mixture from the first reactor to the second reactor.

14. The method of claim 1, wherein the first metal oxidizes in water to yield one or more oxides of the first metal.

15. The method of claim 14, wherein the first metal oxidizes in water to further yield molecular hydrogen.

16. The method of claim 15, wherein the first metal comprises iron.

17. The method of claim 1, wherein the second metal remains substantially unoxidized.

18. The method of claim 1, wherein the second metal catalyzes the reduction of the alkene with molecular hydrogen to yield the alkane.

19. The method of claim 1, wherein the second metal comprises nickel.

20. The method of claim 1, wherein the first metal and the second metal are different.

21. The method of claim 1, wherein separating the alkane from the water comprises mechanical separation.

22. The method of claim 1, wherein the alkene is cyclohexene and the alkane is cyclohexane.

* * * * *